(12) United States Patent
Okada et al.

(10) Patent No.: US 7,799,763 B2
(45) Date of Patent: Sep. 21, 2010

(54) MUSCLE-STRENGTHENING DRUGS AND ANTI-INFLAMMATORY DRUGS

(75) Inventors: Kenkichi Okada, Tokyo (JP); Akio Ochiai, Shimizu (JP); Masaki Kosuge, Shizuoka (JP); Takao Daicho, Shida-gun (JP); Kuniro Tsuji, Shizuoka (JP); Haruo Nukaya, Shimizu (JP); Oto Miura, Musashino (JP)

(73) Assignee: Daicho Kikaku Incorporated Company, Shida-Gun (JP)

( * ) Notice: Subject to any disclaimer, the term of this patent is extended or adjusted under 35 U.S.C. 154(b) by 943 days.

(21) Appl. No.: 11/614,852

(22) Filed: Dec. 21, 2006

(65) Prior Publication Data

US 2007/0129316 A1 Jun. 7, 2007

Related U.S. Application Data

(62) Division of application No. 10/316,849, filed on Dec. 12, 2002, now abandoned.

(51) Int. Cl.
| | |
|---|---|
| *A61K 31/7048* | (2006.01) |
| *A61K 31/353* | (2006.01) |
| *A61K 31/56* | (2006.01) |
| *A61K 31/12* | (2006.01) |

(52) U.S. Cl. .......................... 514/27; 514/456; 514/171; 514/685

(58) Field of Classification Search ................... 514/27, 514/456, 171, 685
See application file for complete search history.

(56) References Cited

U.S. PATENT DOCUMENTS

| | | |
|---|---|---|
| 3,717,470 A | 2/1973 | Yokotsuka et al. |
| 5,776,460 A | 7/1998 | Kim et al. |
| 5,891,924 A | 4/1999 | Aggarwal |
| 6,544,566 B1 | 4/2003 | Waggle et al. |
| 6,793,943 B2 | 9/2004 | Daicho |
| 2002/0028839 A1 | 3/2002 | O'Reilly et al. |

*Primary Examiner*—Jennifer M Kim
(74) *Attorney, Agent, or Firm*—Oliff & Berridge, PLC

(57) ABSTRACT

A muscle-strengthening, anti-inflammatory, antiasthmatic, antidiarrheal or an antidepressant method, or a method for the treatment of diminution of vision, hepatitis, inflammatory intestinal syndrome, functional enteropathy, functional hepatopathy, functional nephropathy, dementia, climacteric symptoms, senile dementia and/or Alzheimer disease, said method comprising: administering to skin a composition comprising (a) at least one member selected from the group consisting of isoflavones and isoflavone glycosides, (b) curcumin, and (c) cholic acid or at least one member selected from the group consisting of scymnol and scymnol esters.

22 Claims, No Drawings

MUSCLE-STRENGTHENING DRUGS AND ANTI-INFLAMMATORY DRUGS

CROSS-REFERENCE TO RELATED APPLICATION

This is a Division of application Ser. No. 10/316,849 filed Dec. 12, 2002, which in turn claims priority under 35 U.S.C. §119 of Japanese Patent Application No. 2001-384849, filed Dec. 18, 2001 in Japan, Japanese Patent Application No. 2002-293899, filed Oct. 7, 2002 in Japan and Japanese Patent Application No. 2002-303877, filed Oct. 18, 2002 in Japan. The disclosures of the prior applications are hereby incorporated by reference herein in their entirety.

TECHNICAL FIELD

The present invention relates to a novel agent or composition for use as a muscle-strengthening drug, an anti-inflammatory drug, an antiasthmatic, an antidiarrheal, an antidepressant, or a drug for the treatment of secondary diseases following cerebral infarction (human stroke sequelae, secondary stroke damages or sequelae of brain infarction), motor paralysis, diminution of vision, hepatitis, inflammatory intestinal syndrome, functional enteropathy, functional cardiopathy, functional hepatopathy, functional nephropathy, dementia, climacteric symptoms, senile dementia and/or Alzheimer disease, and to an agent or composition to be applied to the skin.

BACKGROUND

Serotonin and noradrenaline referred to as brain hormones control satisfaction of the will, and in turn, spiritual satisfaction. In response to satisfaction of the will, voluntary muscles are activated by adrenaline, an adrenal medullary hormone, secreted from adrenal medulla and chromaffin cells on nerve muscles.

Serotonin, noradrenaline and adrenaline are also referred to as biogenic monoamines, and are oxidatively decomposed by an enzyme called monoamine oxidase within as long as 3 hours or reabsorbed into nerve tissues and so forth, resulting in the extinction of most effects of secreted monoamines.

This is an ingenious body mechanism that prevents fatigue produced by the long time action of monoamines.

"KI" (in Japanese; vital energy) refers to all the functions of the human body. Such body's functions are generically classified into 2 types. One function is controlled by autonomic nerves, which are found in various organs, hormone secretions and blood vessels. The other one works for voluntary muscles which act according to commands released from brain thought functions and thought patterns.

It has previously been pointed out that "KI", as represented by "HOKI" (in Japanese; complementing energy) and "RIKI" (in Japanese; circulating energy) in Chinese medicine, indicates only the former functions controlled by autonomic nerves. The commands for "which functions will be activated" and "how they will be exerted" are released from the medulla oblongata located at the lower part of the brain. Considering that "HOKIYAKU" (in Japanese; drug for complementing "KI") activates all functions controlled by autonomic nerves, instead of only activating certain organs and tissues, it is likely that the target point on which the "HOKIYAKU" acts may be medulla oblongata (a source of commands) rather than each organ or tissue. That is, it is concluded that the actions of "HOKIYAKU" are for enhancing and facilitating the emission and transmission of commands from the medulla oblongata.

I have found that the "HOKIYAKU" localizes body blood to various organs. This might be aimed at achieving such a blood localization via, as a result of the blood vessel-dilating and constricting action (one of the important actions of medulla oblongata), not only dilating blood vessels directed to the autonomic nervous control system but also constricting blood vessels directed to the brain and brain-controlled organs whereby more nutrient elements will be delivered to required parts as a secondary action of the "HOKIYAKU".

Further, the onset of depressive syndrome (depression) is caused by retention of a depressive condition when deprived of satisfaction of will and spirit due to a decrease in the secretory capability of biogenic monoamines, whereby the spirit is, on occasion, extremely lowered leading to strong suicidal tendencies.

Until now, for treatment of depression, passive nosotropic therapy has been carried out in which either pharmaceutical drugs which inhibit an action of monoamine oxidase or pharmaceutical drugs which prevent reabsorption of such monoamines are administered so that the concentration of, as a result of decrease in the secretory capability, reduced monoamines would be maintained and an extreme decrease in spirit would be prevented.

However, this therapy is not a fundamental therapy the aim of which is to eliminate the cause of depression, that is, to cure the decreased secretory ability of biogenic monoamines. Thus, it is a therapy in expectation of only naturally recovering the secretion capacity of monoamines over a long period of therapy.

Natural recovery is still a therapy with drawbacks, i.e., not only the secretory ability of monoamines is further decreased due to the continued presence of monoamines, but also physical strength is readily lowered due to fatigue caused by adrenaline-mediated excess burning of sugars and lipids.

It is known in the art that monosaccharides such as glucose and galactose can moisten the skin. However, such monosaccharides are applied by dermal application, hence are readily removed from the skin upon rubbing or washing. It is a problem that such monosaccharides should always be applied.

Proctoptosia, and pains in legs, lumbar regions and arms have occurred with aging. These have been considered to be due only to hematogenous disorders at the respective local sites or resultant inflammation. However, regular dosing of drug products alone which are assumed to be sufficiently capable of eliminating hematogenous disorders has been insufficient in ameliorating such conditions.

These disorders are attributed to insufficient communication of the brain commands to the local sites. Hematogenous disorders and the occurrence of inflammation are problems caused by abnormal motions of muscles due to the incomplete communication of brain commands.

SUMMARY

For instance, although all muscle disorders are not ascribed to insufficient brain communication, it seems that the majority of such disorders are elicited by insufficient communication of brain commands. In particular, it has been found that muscle disorders such as backaches and pains in limbs attributable to aging are easily eliminated by curcumin and others which ameliorate the communication of brain commands.

The present invention has been made to develop pharmaceutical drugs and compositions based on this novel medical theory. An object of the present invention is to provide very effective pharmaceutical drugs and therapeutic compositions having a muscle-strengthening, antiinflammatory, anti-cerebral infarction sequela, anti-motor paralysis, antiasthmatic, anti-vision diminution, antihepatitis, anti-inflammatory intestinal syndrome, anti-functional enteropahy, and/or anti-dementia activity.

In former times, depression was a rare disease. However, the onset rate of depression has recently increased worldwide, and it is said that one in 150 individuals is a depressive patient in the Tokyo Metropolitan Area.

Recently, an interesting opinion has been published concerning the causes for increases in the occurrence of depressive symptoms. Such a theory is as follows:

That is, there has been no war crisis worldwide except in some troubled regions. In addition, social order has been well maintained resulting in reducing opportunities for encountering contingent accidents.

Thus, there has been almost no need for the human body to gird itself and enhance the spirit for such dangers.

Therefore, the need for secretion of biogenic amines has also remarkably decreased, whereby the secretory capability has degenerated with the result that persons would be apt to develop depression.

If this theory is correct, when secretion of biogenic monoamines is artificially stimulated, for example using a secretomotory means once a day, the onset of depression may be prevented, the capability of secreting biogenic monoamines may be recovered even in patients whose secretion capability of biogenic monoamines is lowered, and the patient may recover from depression.

The present invention has been made to develop pharmaceutical drugs and compositions based on such novel medical theory. An object of the present invention is to provide pharmaceutical compositions and therapeutic drugs very effective in the treatment of depression, climacteric disturbance, senile dementia and/or Alzheimer's disease.

A further object of the invention is to provide dermatological agents and compositions, in particular dermatological agents and compositions for external use, which do not directly act on the skin but releases a monosaccharide in vivo after once absorbed into the body and which thus heal a skin injury, prevent skin deterioration or weakening, or restore healthy skin.

The present invention relates to a muscle-strengthening drug or anti-inflammatory drug-containing muscle strengthening drug which comprises isoflavone and/or an isoflavone glycoside, and/or a pungent, bitter or sour substance, and/or cholic acid, and/or scymnol and/or a scymnol ester.

The term "muscle-strengthening drug" used herein refers to an agent acting for reducing muscle fatigue, or increasing muscle strength, for instance. The term "anti-inflammatory drug" used herein refers to an agent for the treatment of inflammation, in particular a therapeutic or prophylactic agent for arthritis, neuralgia or rheumatism, among others.

The present invention relates to a pharmaceutical agent or composition useful as an antiasthmatic, an antidiarrheal, an antidepressant, a drug for the treatment of secondary diseases following cerebral infarction, or a drug for the treatment of motor paralysis, diminution of vision, hepatitis, inflammatory intestinal syndrome, functional enteropathy, functional cardiopathy, functional hepatopathy, functional nephropathy, dementia, climacteric symptoms, senile dementia and/or Alzheimer disease, and to an agent or composition to be applied to the skin.

The drug for inflammatory intestinal syndrome as used herein includes agents for Crohn disease and ulcerative colitis. The anti-functional enteropathy, anti-functional cardiopathy, anti-functional hepatopathy, anti-functional nephropathy and/or antidiarrheal drug as used herein includes anti-irritable bowel syndrome agents.

The antiasthmatic, antidiarrheal, antidepressant, drugs for the treatment of secondary diseases following cerebral infarction, motor paralysis, diminution of vision, hepatitis, inflammatory intestinal syndrome, functional enteropathy, functional cardiopathy, functional hepatopathy, functional nephropathy, dementia, climacteric symptoms, senile dementia and/or Alzheimer disease, and agents or compositions to be applied to the skin as used herein, refer to drugs, agents or compositions/preparations for the prophylaxis and/or treatment of a disease.

DETAILED DESCRIPTION OF EMBODIMENTS

In accordance with the present invention, it is preferable that the pharmaceutical product (or drug) contains a pungent substance, a bitter slubstance, and/or a sour substance. It is more preferable that the pharmaceutical product is in admixture with one or more members selected from the group consisting of isoflavones and isoflavone glycosides. The particularly preferable isoflavone includes soybean isoflavones comprised in soybean. The particularly preferable isoflavone glycoside includes soybean isoflavone glycosides comprised in soybean.

When isoflavone or isoflavone glycoside is administered, it is desirable that the pharmaceutical product is in admixture with one or more members selected from the group consisting of cholic acid, scymnol and scymnol esters.

The daily dose of isoflavone and isoflavone glycoside is preferably 1 to 500 mg, more preferably 5 to 200 mg, and most preferably 10 to 100 mg.

A most preferable pharmaceutical product comprises at least a pungent substance therein.

The pungent substance as used herein includes preferably curcumin

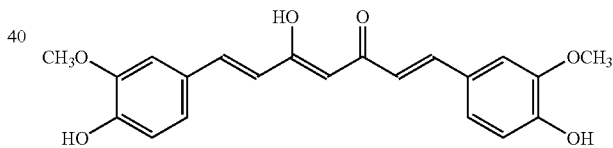

(isolated from Curcumae Rhisoma (root of Curcuma longa L.)), capsaicine

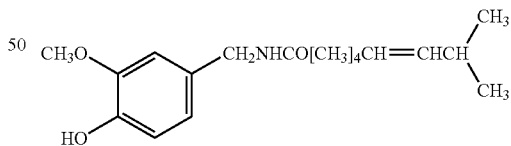

(isolated from fruit of Capsicum annuum L.), piperine

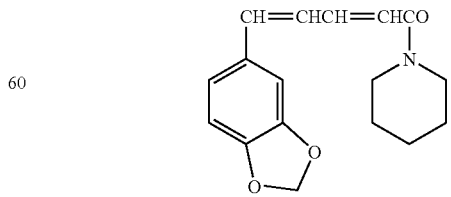

(isolated from black peper (fruit of Piper nigrum L.)), zingerone

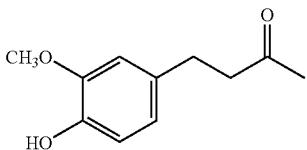

(isolated from ginger root (Zingiber officinale Roscoe)), (6)-shogaol

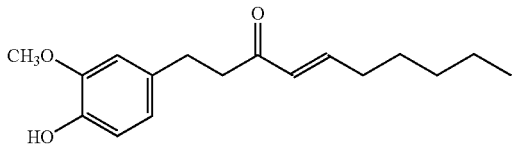

(isolated from ginger root), (6)-gingerol

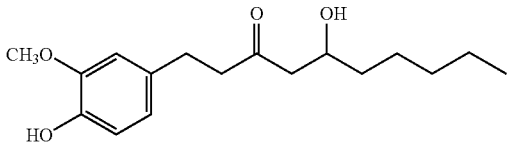

(isolated from ginger root), etc. Among them, curcumin is most preferable.

The bitter substance as used herein includes preferably swertiamarin, gentiopicrin, loganin, etc.

The sour substance as used herein includes preferably citric acid, lactic acid, etc.

The daily dose of the pungent substance is preferably 1 to 1000 mg, more preferably 5 to 300 mg, and most preferably 10 to 70 mg. When it is administered alone, its daily dose is preferably 100 to 800 mg, and most preferably 300 to 500 mg. When it is administered in combination with "KAMPO" pharmaceutical preparations or drugs ("KAMPO", Japan's traditional herbal medicine) having the efficacy of "FUSEI" (as pronounced in Japanese: aid for keeping the body normal), such as JUZEN-TAIHO-TO (as pronounced in Japanese), its daily dose is preferably 100 to 200 mg.

The daily dose of the pungent substance is preferably 1 to 1000 mg, more preferably 10 to 300 mg, and most preferably 20 to 70 mg. When it is administered alone, its daily dose is preferably 100 to 800 mg, and most preferably 300 to 500 mg. When it is administered in combination with "KAMPO" pharmaceutical preparations or drugs having the efficacy of "FUSEI", such as JUZEN-TAIHO-TO (as pronounced in Japanese), its daily dose is preferably 100 to 200 mg.

The daily dose of cholic acid is preferably 1 to 1000 mg, more preferably 2 to 300 mg, and most preferably 10 to 100 mg. The daily dose of scymnol and scymnol esters is preferably 0.1 to 100 mg, more preferably 0.1 to 50 mg, and most preferably 0.3 to 10 mg.

In the case of a preparation to be applied to the skin, it preferably contains a monosaccharide.

The monosaccharide is preferably glucose or galactose, and galactose is more preferred.

The sugar may be a sugar or a sugar acyl ester, and an acyl ester is preferred.

The acyl is preferably a fatty acid acyl, and one to all alcohol moieties may be esterified by an alcohol.

The content of galactose is preferably 0.1% to 30%, more preferably 1% to 5%.

The daily dose of galactose is preferably 0.5 to 500 mg, more preferably 1 to 100 mg.

The content of acetylgalactose is preferably 0.1% to 30%, more preferably 1% to 5%.

The daily dose of acetylgalactose is preferably 0.5 to 500 mg, more preferably 1 to 100 mg.

It is also allowable that the pharmaceutical product is in admixture with other ingredients including not only generic pharmaceutical drugs but also vitamins, anibiotics, anti-cancer drugs, heme Fe, prune extracts (Prunus Domestica fruit extracts), crude drugs (herbal and animal drugs, or galenical preparations; "SHOUYAKU" as pronounced in Japanese), and the like. The "SHOUYAKU" includes preferably those having the efficacy of "FUSEI", for example those capable of activating or stimulating the functions of organs, glands and blood vessels, all controlled by autonomic nerves, those capable of aiding digestion, and others.

The galenical preparations (or crude drugs) of 10 or more kinds have been known as those capable of activating or stimulating the functions of organs, glands and blood vessels, all controlled by autonomic nerves. Examples of such galenical preparations are ginseng (Ginseng Radix, Panax Ginseng), etc. Some of active elements have been revealed for not only ginseng but also such galenical preparations.

Accordingly, such active elements can be preferably admixed therewith. The admixture of such active elements will lead to achievement of activating body-functions.

The particularly preferable galenical preparation include Ginseng (Panax Ginseng or Ginseng Radix), Codonopsitis Radix, Psuodostellariae Radix, American Ginseng, Astragali Radix, Atractylodis Rhizoma, Dioscoreae Rhizoma, Glycyrrhia (Glycyrrhizae Radix), Jujube Fruit (Zizyphi Fructus, Zizyphus vulgaris), Dulcium (malt sugar derived from Oryza seed), Polygonati Rhizoma, Codonopsis lanceolata Benth. et Hock. fil. ("SHIYOUJIN" in Japanese; Oryza sativa L.), etc.

Galenical preparations capable of aiding digestion can be preferably admixed therewith. The particularly preferable galenical preparations capable of aiding digestion include Crataegi Fructus, Massa Medicata Fermentat, Raphani Semen, Fructus Hordei Germinatus, Fructus Oryzae Germinatus ("KOKUGA" in Japanese; Oryza sativa L.), Galli Stomachichum Corium, Asa Foetida, etc.

In the case of dermal preparations, galenical preparations capable of producing a monosaccharide having a body fluid producing activity (so-called "TSUEKI SAYOU" as pronounced in Japanese) or an antianemic or blood activating activity (so-called "HOKETSU KAKKETSU SAYOU" as pronounced in Japanese) is preferably added.

The galenical preparation having body fluid producing activity includes Hoelen (Poria, "BUKURYO" in Japanese; Poria cocus WOLF (Pachyma hoelen RUMPHIUS)), "SEKI-BUKURYO" (in Japanese; pale red portion of Poria cocus), "BUKUSHIN" (in Japanese; particular grade of Poria cocus), "BUKURYOHI" (in Japanese; cortical portion of Poria cocus), etc. The galenical preparation having antianemic or blood-activating activity includes Cnidii Rhizoma ("SEN-KYU in Japanese; Cnidium officinale MAKINO), Salviae Militiorrhiziae Radix ("TANJIN" in Japanese; Salvia miltiorrhiza BUNGE), Mucunae Caulis (Mucuna birdwoodiana, "KEIKETTO" in Japanese; Mucuna birdwoodiana TUTCHER, stem of Millettia reticulata), "MOUTOUSEI" (in Japanese; root of Ilex pubescens), among others.

Scymnol and/or scymnol esters are comprised in biles of shark. Scymnol has the following formula:

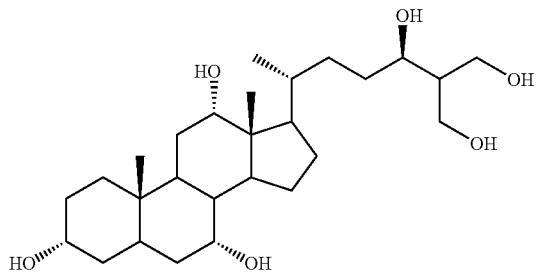

Sodium scymnol sulfate has the following formula:

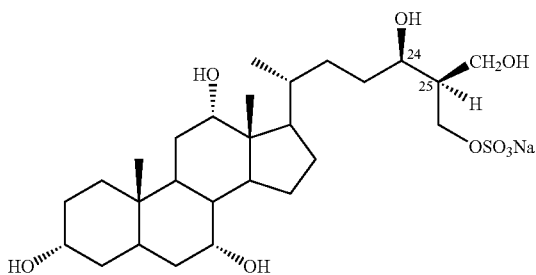

Other materials as used herein include isoflavones and isoflavone glycosides.

For the pharmaceutical products, the active elements contained in soybean are several species of isoflavone glycosides including daidzin, glycitin, genistin, etc. and aglycons thereof, i.e., several species of isoflavones including daidzein, glycitein, genistein, etc.

The soybean is a starting material for producing soybean oil. There is a great demand for soybean oil. Therefore, large amounts of soybean oil are manufactured together with large amounts of by-products, soybean cakes. Although part of such soybean cakes are employed as sources for preparing soybean proteins, etc. which are starting materials for food products, the soybean cake is mainly used for a fertilizer or feed for livestock and its price is therefore extremely low. The soybean cakes which are almost industrial wastes can be used as starting materials to produce inexpensively soybean isoflavones and soybean isoflavone glycosides with high purity.

Preferably, inosic acid is added to the agent or composition of the invention.

Preferably, a fatty acid having an odd number of carbon atoms ("odd-numbered fatty acid") is added to the agent or composition of the invention.

Preferred as the odd-numbered fatty acid are tridecanoic acid, pentadecanoic acid, heptadecanoic acid and nonadecanoic acid. Among them, pentadecanoic acid and heptadecanoic acid are more preferred.

The dosage form of the pharmaceutical agents or composition for use as a muscle-strengthening drug, an anti-inflammatory drug, an antiasthmatic, an antidiarrheal, an antidepressant, or a drug for the treatment of secondary diseases following cerebral infarction, of motor paralysis, diminution of vision, hepatitis, inflammatory intestinal syndrome, functional enteropathy, functional cardiopathy, functional hepatopathy, functional nephropathy, dementia, climacteric symptoms, senile dementia and/or Alzheimer disease, and the agents or compositions to be applied to the skin according to the invention is not particularly limited but may be administered, for example, in the form of such preparations for internal administration or oral route, as tablets, powders, solid preparations or solutions, suppositories or injectable solutions.

An excipient such as lactose or starch, a vegetable oil or the like may also be used.

The dermatological agent or composition according to the invention may be administered in the form of a preparation suitable for external use, and the dosage form thereof is not particularly limited but preferably used in the form of a cream, emulsion, solution or ointment.

The ingredients to be used in the products may be ordinary ones used in conventional creams, emulsions, solutions, or ointments.

EXAMPLES

Described below are examples of the present invention which are provided for illustrative purposes.

Soybean isoflavones and soybean isoflavone glycosides as used in examples are set to be 40% in purity. Cholic acid as used in examples is set to be 90% in purity except for pure cholic acid.

Example 1

Powders

| | |
|---|---|
| Curcumin | 30 mg |
| Scymnol | 1 mg |
| Soybean isoflavone | 125 mg |
| Lactose | 800 mg |
| Cornstarch | qs |
| Magnesium stearate | 10 mg |
| Total | 2000 mg |

(1 g per container (powder paper), twice a day)

A formula except that soybean isoflavone was replaced with soybean isoflavone glycoside was blended to afford powders in the same fashion as above.

Example 2

Granules

| | |
|---|---|
| Curcumin | 30 mg |
| Sodium scymnol sulfate | 1 mg |
| Soybean isoflavone | 125 mg |
| Lactose | 1500 mg |
| Cornstarch | qs |
| Magnesium stearate | 10 mg |
| Total | 2000 mg |

(1 g per container (powder paper), twice a day)

A formula except that soybean isoflavone was replaced with soybean isoflavone glycoside was granulated to afford granules in the same fashion as above.

Example 3

Tablets

| | |
|---|---|
| Curcumin | 30 mg |
| Sodium scymnol sulfate | 1 mg |
| Soybean isoflavone | 125 mg |
| Crystalline cellulose | qs |
| Lactose | 140 mg |
| Magnesium stearate | 6 mg |
| Talc | 3 mg |
| Total | 1120 mg |

(280 mg per tablet, 2 tablets per dose, twice a day)

A formula except that soybean isoflavone was replaced with soybean isoflavone glycoside was compressed to afford tablets in the same fashion as above.

Example 4

Tablets

| | |
|---|---|
| Curcumin | 25 mg |
| Scymnol | 1 mg |
| Soybean isoflavone | 250 mg |
| Ginseng powder | 2000 mg |
| Lactose | 886 mg |
| Crystalline cellulose | qs |
| Carboxymethylcellulose calcium | 320 mg |
| Hydroxypropylcellulose | 558 mg |
| CARPLEX | 30 mg |
| Magnesium stearate | 55 mg |
| Total | 5600 mg |

(280 mg per tablet, 5 tablets per dose, twice a day)

A formula except that soybean isoflavone was replaced with soybean isoflavone glycoside was compressed to afford tablets in the same fashion as above.

Example 5

Hard Capsules

| | |
|---|---|
| Curcumin | 30 mg |
| Scymnol | 1 mg |
| Soybean isoflavone | 125 mg |
| Lactose | 218 mg |
| Cornstarch | qs |
| Magnesium stearate | 6 mg |
| Total | 1150 mg |

(for 4 #1 capsules, 2 capsules per dose, twice a day)

A formula except that soybean isoflavone was replaced with soybean isoflavone glycoside was blended and packed to afford hard capsules in the same fashion as above.

Example 6

Soft Capsules

| | |
|---|---|
| Curcumin | 25 mg |
| Sodium scymnol sulfate | 1 mg |
| Soybean isoflavone | 125 mg |
| Cod liver oil | 80 mg |
| Tocopherol acetate | 5 mg |
| Ginseng extract | 200 mg |
| Yellow beeswax | 55 mg |
| Edible oil | qs |
| Total | 1200 mg |

(4 capsules a day)

A formula except that soybean isoflavone was replaced with soybean isoflavone glycoside was blended and packed to afford soft capsules in the same fashion as above.

Example 7

Drink

| | |
|---|---|
| Curcumin | 30 mg |
| Sodium scymnol sulfate | 1 mg |
| Soybean isoflavone | 125 mg |
| Korean ginseng extract | 10 mg |
| *Rehmanniae Radix* extract (*Rehmannia glutinosa Liboschitz* var. *purpurea Makino*) | 10 mg |
| Royal jelly | 100 mg |
| Thiamin nitrate | 10 mg |
| Riboflavin sodium phosphate | 5 mg |
| Pyridoxine hydrochloride | 10 mg |
| Anhydrous caffeine | 50 mg |
| Ethanol | 1.2 mL |
| Ethyl parahydroxybenzoate | 4 mg |
| Purified water | qs |
| Total | 50 mL/bottle |

A formula except that soybean isoflavone was replaced with soybean isoflavone glycoside was mixed to afford drinks in the same fashion as above.

Example 8

Preparations Admixed with Vitamin, Hard Capsules

| | |
|---|---|
| Curcumin | 25 mg |
| Sodium scymnol sulfate | 1 mg |
| Soybean isoflavone | 125 mg |
| Thiamin hydrochloride | 25 mg |
| Pyridoxine hydrochloride | 10 mg |
| Riboflavin | 10 mg |
| Cyanocobalamin | 12 mg |
| Nicotinamide | 20 mg |
| Calcium pantothenate | 20 mg |
| Ascorbic acid | 60 mg |
| L-cysteine | 10 mg |

| -continued | |
| --- | --- |
| Lactose | 263 mg |
| Magnesium stearate | 6 mg |
| Cornstarch | qs |
| Total | 1150 mg |

(2 capsules per dose, twice a day)

A formula except that soybean isoflavone was replaced with soybean isoflavone glycoside was blended and packed to afford hard capsules in the same fashion as above.

Example 9

Injections

| | |
| --- | --- |
| Curcumin | 30 mg |
| Sodium scymnol sulfate | 1 mg |
| Pure soybean isoflavone | 20 mg |
| Glucose | 500 mg |

The mix was adjusted with 10% sodium hydroxide as a pH regulator to pH 7. Next, distilled water for injection was added to the mix to make the total volume 5 ml. The resultant mix was dispensed into each ampule which was then melt-sealed, and sterilized.

A formula except that soybean isoflavone was replaced with soybean isoflavone glycoside was blended to afford injections in the same fashion as above.

Example 10

Powders

| | |
| --- | --- |
| Curcumin | 30 mg |
| Cholic acid | 60 mg |
| Soybean isoflavone glycoside | 125 mg |
| Lactose | 2700 mg |
| Cornstarch | qs |
| Light anhydrous silicic acid | 5 mg |
| Magnesium stearate | 10 mg |
| Total | 4000 mg |

(2 g per container (powder paper), twice a day)

A formula except that soybean isoflavone glycoside was replaced with soybean isoflavone was blended to afford powders in the same fashion as above.

Example 11

Granules

| | |
| --- | --- |
| Curcumin | 25 mg |
| Cholic acid | 60 mg |
| Soybean isoflavone glycoside | 125 mg |
| Lactose | 2700 mg |
| Cornstarch | qs |
| Crystalline cellulose | 300 mg |
| Light anhydrous silicic acid | 5 mg |
| Magnesium stearate | 10 mg |
| Total | 4000 mg |

(2 g per container (powder paper), twice a day)

A formula except that soybean isoflavone glycoside was replaced with soybean isoflavone was granulated to afford granules in the same fashion as above.

Example 12

Spherical Granules

| | |
| --- | --- |
| Curcumin | 30 mg |
| Cholic acid | 60 mg |
| Soybean isoflavone glycoside | 125 mg |
| Lactose | 515 mg |
| Cornstarch | qs |
| "KAN-BAI-KO" (in Japanese) (*Prunus mume* fruit powder) | 500 mg |
| Crystalline cellulose | 400 mg |
| Total | 2000 mg |

(1 g per container (powder paper), twice a day)

A formula except that soybean isoflavone glycoside was replaced with soybean isoflavone was granulated to afford spherical granules in the same fashion as above.

Example 13

Tablets

| | |
| --- | --- |
| Curcumin | 30 mg |
| Cholic acid | 140 mg |
| Soybean isoflavone glycoside | 280 mg |
| Lactose | 4000 mg |
| Carboxymethylcellulose calcium | 320 mg |
| Hydroxypropylcellulose | 74 mg |
| Crystalline cellulose | qs |
| CARPLEX | 30 mg |
| Magnesium stearate | 10 mg |
| Total | 5484 mg |

(280 mg per tablet, 5 tablets per dose, twice a day)

A formula except that soybean isoflavone glycoside was replaced with soybean isoflavone was compressed to afford tablets in the same fashion as above.

Example 14

Hard Capsules

| | |
| --- | --- |
| Curcumin | 25 mg |
| Cholic acid | 60 mg |
| Soybean isoflavone glycoside | 125 mg |
| Cornstarch | qs |
| Magnesium stearate | 9 mg |
| Total | 1153 mg |

(#1 capsule, 4 capsules a day)

A formula except that soybean isoflavone glycoside was replaced with soybean isoflavone was blended and packed to afford hard capsules in the same fashion as above.

Example 15

Soft Capsules

| | |
|---|---|
| Curcumin | 30 mg |
| Cholic acid | 60 mg |
| Soybean isoflavone glycoside | 125 mg |
| Yellow beeswax | 55 mg |
| Edible oil | qs |
| Total | 1200 mg |

(4 capsules for a daily dose)

A formula except that soybean isoflavone glycoside was replaced with soybean isoflavone was blended and packed to afford soft capsules in the same fashion as above.

Example 16

Injections

| | |
|---|---|
| Curcumin | 25 mg |
| Pure cholic acid | 20 mg |
| Pure soybean isoflavone glycoside | 20 mg |
| Glucose | 1000 mg |
| Sodium carbonate (pH regulator) | qs |

Distilled water for injection was added to the mix until the total volume reached 5 ml.

A formula except that soybean isoflavone glycoside was replaced with soybean isoflavone was blended to afford injections in the same fashion as above.

Example 17

Drink

| | |
|---|---|
| Curcumin | 30 mg |
| Cholic acid | 60 mg |
| Soybean isoflavone glycoside | 125 mg |
| Korean ginseng extract | 1500 mg |
| *Euphoria longan* extract | 100 mg |
| *Schizandrae Fructus* fluid extract (fruit of *Schizandra chinensis* Baill.) | 300 mg |
| Royal jelly | 150 mg |
| Riboflavin sodium phosphate | 10 mg |
| Ethanol | 1.2 ml |
| Parahydroxybenzoic acid | 4 mg |
| Purified water | qs |
| Total | 50 ml |

A formula except that soybean isoflavone glycoside was replaced with soybean isoflavone was mixed to afford drinks in the same fashion as above.

Example 18

Granules

| | |
|---|---|
| Curcumin | 25 mg |
| Cholic acid | 60 mg |
| Soybean isoflavone glycoside | 125 mg |
| Thiamin hydrochloride | 10 mg |
| Pyridoxine hydrochloride | 100 mg |
| Hydroxocobalamin hydrochloride | 1.027 mg |
| Tocopherol acetate | 100 mg |
| Lactose | 2700 mg |
| Crystalline cellulose | 300 mg |
| Light anhydrous silicic acid | 5 mg |
| Magnesium stearate | 10 mg |
| Cornstarch | qs |
| Total | 4000 mg |

(2 g per container (powder paper), twice a day)

A formula except that soybean isoflavone glycoside was replaced with soybean isoflavone was granulated to afford granules in the same fashion as above.

Example 19

Capsules

| | |
|---|---|
| Curcumin | 30 mg |
| Cholic acid | 60 mg |
| Soybean isoflavone glycoside | 125 mg |
| Vitamin A oil | 4 mg |
| Cholecalciferol | 0.005 mg |
| Tocopherol acetate | 10 mg |
| Vitamin C | 600 mg |
| Crystalline cellulose | 250 mg |
| Magnesium stearate | 6 mg |
| Cornstarch | qs |
| Total | 1150 mg |

(for 4 #1 capsules, 2 capsules per dose, twice a day)

A formula except that soybean isoflavone glycoside was replaced with soybean isoflavone was blended and packed to afford capsules in the same fashion as above.

Example 20

Capsules

| | |
|---|---|
| Curcumin | 25 mg |
| Cholic acid | 60 mg |
| Soybean isoflavone glycoside | 125 mg |
| Cephalexin | 375 mg |
| Cornstarch | qs |
| Magnesium stearate | 6 mg |
| Total | 855 mg |

(for 3 #2 capsules)

A formula except that soybean isoflavone glycoside was replaced with soybean isoflavone was blended and packed to afford capsules in the same fashion as above.

Example 21

Soft Capsules

| | |
|---|---|
| Curcumin | 25 mg |
| Sodium scymnol sulfate | 1 mg |
| Soybean isoflavone | 125 mg |
| Cod liver oil | 80 mg |
| Tocopherol acetate | 5 mg |
| Heptadecanoic acid | 30 mg |
| Inosinic acid | 100 mg |
| Ginseng extract | 200 mg |
| Yellow beeswax | 55 mg |
| Edible oil | qs |
| Total | 1200 mg |

(4 capsules a day)

A formula except that soybean isoflavone was replaced with soybean isoflavone glycoside was blended and packed to afford soft capsules in the same fashion as above.

Example 22

Soft Capsules

| | |
|---|---|
| Curcumin | 30 mg |
| Cholic acid | 60 mg |
| Soybean isoflavone glycoside | 125 mg |
| Heptadecanoic acid | 30 mg |
| Inosinic acid | 100 mg |
| Yellow beeswax | 55 mg |
| Edible oil | qs |
| Total | 1200 mg |

(4 capsules a day)

A formula except that soybean isoflavone glycoside was replaced with soybean isoflavone was blended and packed to afford soft capsules in the same fashion as above.

Example 23

Powders

| | |
|---|---|
| Scymnol | 1 mg |
| Soybean isoflavone | 125 mg |
| Lactose | 800 mg |
| Cornstarch | qs |
| Magnesium stearate | 10 mg |
| Total | 2000 mg |

(1 g per container (powder paper), twice a day)

A formula except that soybean isoflavone was replaced with soybean isoflavone glycoside was blended to afford powders in the same fashion as above.

Example 24

Granules

| | |
|---|---|
| Sodium scymnol sulfate | 1 mg |
| Soybean isoflavone | 125 mg |
| Lactose | 1500 mg |
| Cornstarch | qs |
| Magnesium stearate | 10 mg |
| Total | 2000 mg |

(1 g per container (powder paper), twice a day)

A formula except that soybean isoflavone was replaced with soybean isoflavone glycoside was granulated to afford granules in the same fashion as above.

Example 25

Tablets

| | |
|---|---|
| Sodium scymnol sulfate | 1 mg |
| Soybean isoflavone | 125 mg |
| Crystalline cellulose | qs |
| Lactose | 140 mg |
| Magnesium stearate | 6 mg |
| Talc | 3 mg |
| Total | 1120 mg |

(280 mg per tablet, 2 tablets per dose, twice a day)

A formula except that soybean isoflavone was replaced with soybean isoflavone glycoside was compressed to afford tablets in the same fashion as above.

Example 26

Hard Capsules

| | |
|---|---|
| Scymnol | 1 mg |
| Soybean isoflavone | 125 mg |
| Lactose | 218 mg |
| Cornstarch | qs |
| Magnesium stearate | 6 mg |
| Total | 1150 mg |

(for 4 #1 capsules, 2 capsules per dose, twice a day)

A formula except that soybean isoflavone was replaced with soybean isoflavone glycoside was blended and packed to afford hard capsules in the same fashion as above.

Example 27

Soft Capsules

| | |
|---|---|
| Sodium scymnol sulfate | 1 mg |
| Soybean isoflavone | 125 mg |
| Cod liver oil | 80 mg |
| Tocopherol acetate | 5 mg |
| Ginseng extract | 200 mg |
| Yellow beeswax | 55 mg |
| Edible oil | qs |
| Total | 1200 mg |

(4 capsules a day)

A formula except that soybean isoflavone was replaced with soybean isoflavone glycoside was blended and packed to afford soft capsules in the same fashion as above.

Example 28

Drink

| | |
|---|---|
| Sodium scymnol sulfate | 1 mg |
| Soybean isoflavone | 125 mg |
| Korean ginseng extract | 10 mg |
| Rehmanniae Radix extract | 10 mg |
| Royal jelly | 100 mg |
| Thiamin nitrate | 10 mg |
| Riboflavin sodium phosphate | 5 mg |
| Pyridoxine hydrochloride | 10 mg |
| Anhydrous caffeine | 50 mg |
| Ethanol | 1.2 mL |
| Ethyl parahydroxybenzoate | 4 mg |
| Purified water | qs |
| Total | 50 mL/bottle |

A formula except that soybean isoflavone was replaced with soybean isoflavone glycoside was mixed to afford drinks in the same fashion as above.

Example 29

Injectable Solution

| | |
|---|---|
| Sodium scymnol sulfate | 1 mg |
| Purified soybean isoflavone | 20 mg |
| Glucose | 500 mg |

The pH is adjusted to 7 with 10% sodium hydroxide for pH adjustment, distilled water for injection is added to make the total amount 5 mL, and an ampoule filled therewith is sealed and sterilized.

An injectable solution was produced in the same manner using soybean isoflavone glycoside in lieu of soybean isoflavone.

Example 30

Nourishing Cream (O/W)

| | | |
|---|---|---|
| (A) | POE(40) monostearate | 3.0 g |
| | Sorbitan monopalmitate | 1.0 g |
| | Cetyl isooctanoate | 10.0 g |
| | Isopropyl myristate | 5.0 g |
| | Liquid paraffin (#70) | 5.0 g |
| | MC stearic acid | 10.0 g |
| | Cetanol | 3.0 g |
| | Paraffin wax (135° F.) | 3.0 g |
| | Dehydrated lanoline | 2.0 g |
| | Pyridoxine dipalmitate | 0.3 g |
| | Methylparaben | 0.1 g |
| | Butylparaben | 0.1 g |
| | Cholic acid | 0.1 g |
| | Soybean isoflavone (on 100% purity basis) | 0.5 g |
| | Acetylgalactose | 2.0 g |
| | Curcumin | 0.1 g |
| (B) | Borax | 0.5 g |
| | Propylene glycol | 5.0 g |
| | Purified water | q.s. |
| | Total | 100.0 g |
| (C) | Perfume | 0.3 to 0.6 g |

Example 31

Emulsions

| | | |
|---|---|---|
| (A) | POE(20) behenyl ether | 2.4 g |
| | Sorbitan monopalmitate | 1.6 g |
| | Isostearyl palmitate | 5.0 g |
| | Isopropyl myristate | 3.0 g |
| | Dehydrated lanoline | 1.5 g |
| | MC stearic acid | 1.0 g |
| | Cetanol | 1.0 g |
| | Beeswax | 2.0 g |
| | Paraffin wax (135° F.) | 2.0 g |
| | Spermaceti | 2.0 g |
| | Methylparaben | 0.1 g |
| | Butylparaben | 0.1 g |
| | Cholic acid | 0.1 g |
| | Acetylgalactose | 2.0 g |
| | Curcumin | 0.1 g |
| (B) | Borax | 0.5 g |
| | Carbopol 940 (2% aqueous solution) | 10.0 g |
| | Propylene glycol | 10.0 g |
| | Soybean isoflavone (on 100% purity basis) | 0.1 g |
| | Galactose | 2.0 g |
| | Purified water | q.s. |
| | Total | 100.0 g |
| (C) | Perfume | 0.2 to 0.4 g |

Example 32

Nourishing Cream (W/O)

| | | |
|---|---|---|
| (A) | POE(15) glycerol vegetable oil fatty acid ester | 1.5 g |
| | Sorbitan sesquioleate | 3.5 g |
| | Isopropyl myristate | 10.0 g |
| | Liquid paraffin (#70) | 10.0 g |
| | Cetanol | 4.0 g |
| | Paraffin wax (135° F.) | 5.0 g |
| | Beeswax | 10.0 g |
| | Methylparaben | 0.1 g |

-continued

|  |  |  |
|---|---|---|
|  | Butylparaben | 0.1 g |
|  | Cholic acid | 0.5 g |
|  | Acetylgalactose | 2.0 g |
|  | Curcumin | 0.1 g |
| (B) | Borax | 0.5 g |
|  | Propylene glycol | 2.0 g |
|  | Soybean isoflavone (on 100% basis) | 1.0 g |
|  | Purified water | q.s. |
|  | Total | 100.0 g |
| (C) | Perfume | 0.3 to 0.5 g |

Example 33

Cold Cream (W/O)

|  |  |  |
|---|---|---|
| (A) | POE(6)sorbitan monooleate | 1.0 g |
|  | Sorbitan monoisostearate | 4.0 g |
|  | Batyl monoisostearate | 1.0 g |
|  | Liquid paraffin (#70) | 25.0 g |
|  | Lanoline alcohol | 4.0 g |
|  | Beeswax | 15.0 g |
|  | Paraffin wax (135° F.) | 5.0 g |
|  | Methylparaben | 0.1 g |
|  | Butylparaben | 0.1 g |
|  | Acetylgalactose | 2.0 g |
|  | Soybean isoflavone (on 100% purity basis) | 0.1 g |
|  | Cholic acid | 0.1 g |
| (B) | Borax | 0.8 g |
|  | Purified water | q.s. |
|  | Total | 100.0 g |
| (C) | Perfume | 0.3 to 0.5 g |

No studies have been conducted on the efficacy of curcumin, zingerone, or shogaol on the stimulation of adrenaline secretion. However, the secretomotory actions on adrenaline have been clarified through animal experiments using mice in which blood glucose levels were remarkably elevated.

Tablets of Example 4 were administered once a day.

For an eighty-three year old male afflicted with walking difficulties and severe anal prolapse, occurred as he was aging, the dosing led to easy mobility and recovery from proctoptosia, with a clear feeling that the anal sphincter functioned. One-month dosing led to clear amelioration of his conditions.

For a male (age 63) afflicted with difficulty in walking up and down stairs, the dosing led to easy movement on staircases. One-month dose trials led to clear amelioration. The tablet of example 13 has a similar efficacy.

If these results were simply attributable to pharmacological action to improve local muscle activity, such information would be contained in European and American data and in results found in Okinawa, wherein curcumin is applied. No such data exists therein. This indicates that these results might be attributed to improvements in brain communication of commands (released as a result of brain thought) to local sites.

In Western medicine, it has been understood that proctoptosia and leg, lumbus and arm aches are attributable only to hematogenous disorders and resultant inflammation at local sites. However, these pathological conditions were not significantly ameliorated by a single regular dose of drugs admixed with one of scymnol, isoflavone, and cholic acid which are significantly capable of removing hematogenous disorders. Thus, it can be understood that these disorders are attributed to insufficient communication of brain commands to local sites and therefore the hematogenous disorders and onset of inflammation are problems caused by abnormal motions of muscles due to incomplete communication of brain commands.

When male and female patients (5 each, age 60 to 75) complained of backaches, limb pains and muscle disorders such as proctoptosia (which occurred as they were aging) took doses, such clinical conditions were alleviated or cured.

Although all muscle disorders are not ascribable to insufficient brain communication, it seems that the majority of such disorders are elicited by insufficient communication of brain commands.

Coadministration of isoflavone, cholic acid, scymnol, curcumin and so on enables the removal of muscle disorders as such components have the stimulating actions on brain activity. This is good news to the elders for both physical and mental rejuvenation. These formulations are extremely effective for arthritis such as rheumatism and in particular, greatly influence the prevention.

Curcumin is readily available. For instance, highlypure curcumin is on the market.

Capsaicine (30 mg) instead of curcumin preparations of Example 1 was administered to elderly patients between the ages of 76 and 83 once daily. Several days later, its effects were dramatic. It has been proved that the drug is effective for muscular degeneration, arthritis and rheumatism after one week. Capsaicine is a powerful irritant with burning aftertaste.

Administration of the agent or composition of Example 6 produced the following effects.

When the drug was administered to a 74-year-old female, her lumbargo was cured in 6 weeks. After the inventive drug was administered to a 39-year-old woman for 6 weeks, her headache vanished. In a 56-year-old woman, one week administration resulted in recovery from her rheumaotid arthritis. When it was administered to a 70-year-old woman, her arthralgia and pain in osteomere disappeared in 2 weeks. After the drug was administered to a 59-year-old woman for 6 weeks, her painful stiffness in neck and shoulder was obviated.

The capsule of Example 6 was given once daily, producing the following effects.

In a 39-year-old woman complaining of cold feeling, headache and diminution of vision, such symptoms disappeared after the drug was administered for 6 weeks. In a 53-year-old woman with arrhythmia, a marked relief was attained after the pharmaceutical preparation was administered for 1 year. In a 71-year-old man with sequela following cerebral infarction and with motor paralysis in the left side of the body, the treated conditions were alleviated after the pharmaceutical preparation was administered for 8 weeks. In a 66-year-old woman with sequela following cerebral infarction and with motor paralysis in the left side of the body, the conditions were markedly ameliorated after the pharmaceutical preparation was administered for 8 weeks. In a 73-year-old woman with sequela following cerebral infarction and with motor paralysis in the left side of the body, the treated conditions were markedly ameliorated after the pharmaceutical preparation was administered for 8 weeks. In a 43-year-old woman with paroxysmal positional nystagmus, the conditions were alleviated after the pharmaceutical preparation was administered for 6 weeks. In a 64-year-old woman with asthma, the symptoms were significantly ameliorated after the pharmaceutical reparation was administered for 4 weeks.

In a 25-year-old man with irritable colitis, the treated condition was cured after the drug was administered for 4 weeks.

In a 32-year-old man with irritable colitis, the condition was ameliorated after administration over 4 weeks. In a 66-year-old man with gastric ulcer and diarrhea, the treated conditions were cured after administration for 2 weeks. In a 66-year-old woman with diarrhea, the treated condition was cured after administration for 4 weeks. In a 29-year-old woman with ulcerative colitis, the disease was cured after administration for 1 week. In a 42-year-old woman with diarrhea and feeling of cold, the conditions were cured after administration for 8 weeks. In a man with repeated diarrhea and constipation, the symptoms were cured. In a 36-year-old man with Crohn disease, the disease was cured after administration for 3 weeks. When the drug was administered to a 48-year-old man with hepatitis for 2 weeks, the disease was cured. In a 48-year-old woman with chromic nephritis, the diseases were markedly alleviated after administration for 6 weeks.

In a 64-year-old woman with hypothyroidism, the treated condition was ameliorated after administration over 16 weeks. In a 39-year-old woman with feeling of cold, fatigability, headache and diminution of vision, the conditions were cured after administration for 6 weeks. In a 74-year-old woman with lumbargo, abdominal pain and amnesia, the treated conditions were ameliorated after administration for 6 weeks. In a 60-year-old woman with edema, lumbargo and pain in the knee, the diseases were markedly alleviated after administration for 12 weeks. In a 39-year-old woman with feeling of cold and fatigability, the symptoms were obviated after administration for 6 weeks. In a 71-year-old woman with vertigo and tinnitus, the diseases were alleviated in 6 weeks. In a 41-year-old woman with chromic fatigue, the symptom was alleviated after administration for 6 weeks. In a 54-year-old woman with chronic fatigue syndrome, the conditions were alleviated after administration for 17 weeks. In a 47-year-old man with chronic fatigue, the treated condition was relieved after administration for 6 weeks. In a 72-year-old man in a subvirile condition, the treated symptom was cured after the preparation was administered for 8 weeks. In a 71-year-old woman with tinnitus and feeling of fatigue, the conditions were ameliorated after the preparation was administered for 9 weeks. In a 43-year-old woman with paroxysmal positional nystagmus, the symptom was ameliorated after the preparation was administered for 6 weeks. In a 54-year-old woman with chronic fatigue syndrome, the conditions were alleviated after the preparation was administered for 17 weeks. After administration over a period of 16 weeks, a relief was achieved in a 50-year-old man complaining of weariness and enervation. In a 75-year-old woman (an atomic bomb victim) with lung cancer and senile dementia, the conditions were relieved and the side effects of drugs for lung cancer and atomic bomb syndrome were alleviated after the preparation was administered for 4 weeks. In a 36-year-old woman complaining of enervation and physical weakness, the conditions were ameliorated after administration for 12 weeks. In a 71-year-old man with senile dementia, the disease was cured after the preparation was administered for 9 weeks. In a 75-year-old woman with senile dementia, the disease was alleviated after administration for 4 weeks. In a 60-year-old woman with lacunar dementia, the treated condition was cured after the preparation was administered for 12 weeks.

In a 34-year-old woman with lung cancer and brain tumor, the treated conditions were alleviated significantly after the preparation was administered for 4 weeks. In a 51-year-old woman with breast cancer and lymphoma, the treated conditions were alleviated remarkably after administration over a period of 2 weeks.

After the capsule preparation of Example 6 was administered over a period of 16 weeks, the following effects were produced as for hair, for instance.

In a 62-year-old silver-haired man, black hair grew along the hairline. In a 61-year-old man, the sideburns and the hair in the middle of forehead became black. In a 55-year-old man, two black hairs grew in the forehead. In a 68-year-old woman, black hair grew along the forehead line, and the hair on the forearm became abnormally long. The hair growth phenomenon was remarkable in the left side of the body. In a 68-year-old woman, the hair became black like a wig along the forehead line. In an 82-year-old woman, her eyebrows became thick. In a 55-year-old man, 9 to 12 black hairs grew along his receding forehead line. In a 64-year-old woman, hair grew and her verrucae disappeared. In a 74-year-old woman, her eyebrows became black. In a 64-year-old woman with hypothyroidism and alopecia, the treated conditions were cured after the preparation was administered for 16 weeks. When a 74-year-old healthy woman receive the preparation for 16 weeks, her alopecia was cured by the administration. In a 34-year-old woman with lung cancer and brain tumor, a marked relief was produced with respect to alopecia due to adverse effects of cancer therapy. In a 69-year-old woman with vitiligo, the skin became reddened after the preparation was administered for 2 weeks. In a 55-year-old woman with vitiligo, a relief was brought about after administration for 4 weeks.

Similarly, it has also been verified that the instant products have skin beautifying actions and pharmacological actions such as therapeutic or prophylactic actions against atopic dermatitis, various types of dermatitis, dermatomycosis, verrucosis, pigmentation, vulgar psoriasis, senile xeroderma, senile keratoma, and skin injuries, and hair-restoring, peptic juice secretion promoting, perspiration promoting, lapactic, diuretic and other actions.

Tablets (250 mg each) containing curcumin (15 mg), cholic acid (20 mg) and soybean isoflavone glycoside (40 mg) in admixture with lactose were administered at a dose of 3 tablets a day (at a dose of 45 mg of curcumin once a day) to 10 patients who had regularly received drugs having the efficacy of "FU-SEI" (in Japanese). The results are shown in the following Table:

TABLE 1

| | Age | Sex | Pathological State | Drug Regularly Dosed | | | | Efficacy |
| | | | | Antidepressant | Tranquilizer | Hypnotic | Hospitalization | |
|---|---|---|---|---|---|---|---|---|
| 1 | 51 | Male | Severe Depression, Anxiety | ○ | ○ | ○ | ○ | ◉ |
| 2 | 38 | Male | Insomnia, Anxiety, Irritableness | ○ | ○ | ○ | ○ | ○ |
| 3 | 51 | Male | Insomnia, Anxiety | X | X | X | X | — |
| 4 | 30 | Female | Insomnia, Anxiety, Depression | ○ | ○ | ○ | X | ◉ |
| 5 | 18 | Female | Insomnia, Anxiety, Irritableness | X | X | X | X | ◉ |

TABLE 1-continued

| | Age | Sex | Pathological State | Drug Regularly Dosed | | | | Efficacy |
| | | | | Antidepressant | Tranquilizer | Hypnotic | Hospitalization | |
|---|---|---|---|---|---|---|---|---|
| 6 | 76 | Male | Irritableness | X | X | X | X | ○ |
| 7 | 74 | Female | Intensive Anxiety, Insomnia, Irritableness | X | X | X | X | ○ |
| 8 | 48 | Female | Depression, Excessive sleeping | ○ | ○ | X | X | ◎ |
| 9 | 48 | Male | Psychoactor detardation, Irritableness, Intensive Depression | X | X | X | X | ◎ |
| 10 | 39 | Female | Intensive Depression, Insomnia, Anxiety | X | X | X | X | ◎ |

All patients were diagnosed as suffering from depression by specialized physicians.
For efficacy: ○, effective: ◎, significantly effective: —, follow-up As shown in the above Table, the drug is effective in 90% of the cases and the significantly effective case equals 60%.

These good results indicate the possibility of recovery from depression which had been said to be a non-curable disease. The examples as disclosed in the Table show results obtained from dosage trials over two months after the initiation of administration; however, long term observation is required for recurrence of depression. Thus, it has been proven that many curcumin-dosed patients are able to return to daily life routines nearly identical to those of ordinary people (non-sufferers of depression), demonstrating that these antidepressants of the present invention are extremely effective in treating depression.

When tablets (250 mg each) containing, in admixture with lactose, sodium scymnol sulfate (1 mg) in place of cholic acid were administered, similar results were obtained.

Similarly, granules of Examples 2 and 11 were administered to 12 and 14 females with menopausal disorders including broodiness, depression and dizziness, etc., respectively, at 45 mg of curcumin per day. Five days after the dosing, the broodiness, depression and dizziness were mitigated in five and six individuals, respectively. Three weeks later, improvements were seen in 11 and 12 individuals, respectively.

When the preparation was administered to 10 forgetful patients just in a preliminary step of senile dementia, the forgetfulness was alleviated in 7 patients. The preparation was also useful in the treatment of Alzheimer disease.

When granules of Example 2 were administered to 10 elderly patients in the preliminary stages of senile dementia, memory loss was ameliorated in 7 individuals. When granules of Example 11 were administered, similar results were obtained. Such products are also effective for Alzheimer's disease.

After the preparation of Example 7 was administered to a 51-year-old man with a tendency toward depression, weariness and enervation over a period of 16 weeks, the treated states were alleviated. In a 38-year-old woman with autonomic nervous system excitement, enervation and poor physical strength, the treated conditions were alleviated after administration for 2 weeks. After the preparation was administered to a 59-year-old woman with sever emaciation following hysterectomy for 6 weeks, the treated conditions were alleviated significantly. After the preparation was administered to a 46-year-old woman with anemia and hemorrhoid, for 8 weeks, the treated symptoms were remarkably alleviated. When the inventive preparation was administered to a 71-year-old man with sequela of cerebral infarction and with senile dementia for 10 weeks, the treated conditions were significantly relieved.

Curcumin is readily available. For instance, highly pure curcumin is on the market.

Capsules wherein powders produced by admixture of capsaicine (50 mg) with lactose were packed in combination with isoflavone glycoside and cholic acid were administered to patients with depression once daily. Several days later, effects were dramatic. The patient were nearly completely recovered from depression after a week. Capsaicine is a powerful irritant with burning aftertaste.

ADVANTAGES OF THE PRESENT INVENTION

The present invention is very effective and advantageous in that it can provide pharmaceutical agents or compositions useful as muscle-strengthening drugs, anti-inflammatory drugs, antiasthmatics, antidiarrheals, antidepressants, or drugs for the treatment of secondary diseases following cerebral infarction, motor paralysis, diminution of vision, hepatitis, inflammatory intestinal syndrome, functional enteropathy, functional cardiopathy, functional hepatopathy, functional nephropathy, dementia, climacteric symptoms, senile dementia and/or Alzheimer disease, and dermatological agents or compositions suitable for skin applications, which can treat or prevent muscle weakening and inflammation, in particular arthritis and rheumatism, by the synergistic action resulting from administration of isoflavone, cholic acid or scymnol, and a pungent, bitter or sour substance, in particular a pungent substance.

When used as an agent for skin use, the composition can produce good cosmetic effects such as whitening, blotch-removing, wrinkle-removing, trichogenous and/or hair-restoring effects, as well as skin beautifying effects and pharmacological effects such as therapeutic effects against atopic dermatitis, various types of dermatitis, dermatomycosis, verrucosis, pigmentation, vulgar psoriasis, senile xeroderma, senile keratoma, and skin injuries, and hair-restoring, peptic juice secretion promoting, perspiration promoting, lapactic, diuretic and other effects.

The agent or composition is also advantageously effective in preventing adverse effects of anticancer drugs, namely depilation, internal hemorrhage, diarrhea, and disorders of heart, liver, kidney, etc. Therefore, when used in combination with an anticancer drug, it can suppress those side effects otherwise produced by such drugs.

What is claimed is:

1. A method of treating depression in a patient in need thereof comprising administering an effective amount of a composition comprising (a) at least one member selected from the group consisting of soybean isoflavones and soybean isoflavone glycosides, (b) curcumin, and (c) cholic acid or at least one member selected from the group consisting of scymnol and scymnol esters.

2. The method of claim 1, comprising administering a daily dose of 1-500 mg of the isoflavones or isoflavone glycosides.

3. The method of claim 1, comprising administering a daily dose of 5-200 mg of the isoflavones or isoflavone glycosides.

4. The method of claim 1, comprising administering a daily dose of 10-100 mg of the isoflavones or isoflavone glycosides.

5. The method of claim 1, comprising administering a daily dose of 1-1000 mg of the curcumin.

6. The method of claim 1, comprising administering a daily dose of 5-300 mg of the curcumin.

7. The method of claim 1, comprising administering a daily dose of 20-70 mg of the curcumin.

8. The method of claim 1, comprising administering a daily dose of 10-70 mg of the curcumin.

9. The method of claim 1, comprising administering curcumin with at least one member selected from the group consisting of KAMPO and FUSEI.

10. The method of claim 9, comprising administering a daily dose of 100-200 mg of the curcumin.

11. The method of claim 1, wherein the composition includes cholic acid.

12. The method of claim 11, comprising administering a daily dose of 1-1000 mg of the cholic acid.

13. The method of claim 11, comprising administering a daily dose of 2-300 mg of the cholic acid.

14. The method of claim 11, comprising administering a daily dose of 20-70 mg of the cholic acid.

15. The method of claim 1, wherein the composition includes scymnol or scymnol esters.

16. The method of claim 15, comprising administering a daily dose of 0.1-100 mg of the scymnol or scymnol esters.

17. The method of claim 15, comprising administering a daily dose of 0.1-50 mg of the scymnol or scymnol esters.

18. The method of claim 15, comprising administering a daily dose of 0.3-10 mg of the scymnol or scymnol esters.

19. The method of claim 1, wherein the composition further comprises at least one monosaccharide.

20. The method of claim 19, wherein the at least one monosaccharide is galactose or acetylgalactose.

21. The method of claim 20, comprising administering a daily dose of 0.5-500 mg of the at least one monosaccharide.

22. The method of claim 20, comprising administering a daily dose of 1-100 mg of the at least one monosaccharide.

* * * * *